United States Patent [19]

Hydro

[11] Patent Number: 4,558,160

[45] Date of Patent: Dec. 10, 1985

[54] PRODUCTION OF DICHLOROFORMOXIME

[76] Inventor: William R. Hydro, 1309 Saratoga Dr., Bel Air, Md. 21014

[21] Appl. No.: 603,847

[22] Filed: Apr. 25, 1984

[51] Int. Cl.$^4$ ........................................... C07C 131/00
[52] U.S. Cl. ..................................................... 564/261
[58] Field of Search ....................................... 564/261

[56] References Cited

PUBLICATIONS

Chiesa, Peter P., Report CRLR 322, Project No. 4-0-8-03-001 (1954), Army Chemical Center, Maryland.
Gryzskiewicz-Trochimowski, E. et al., *Chemical Abstracts*, vol. 42 (1948), #8165a.

*Primary Examiner*—Natalie Trousof
*Assistant Examiner*—L. Hendriksen
*Attorney, Agent, or Firm*—Dressler, Goldsmith, Shore, Sutker & Milnanow, Ltd.

[57] ABSTRACT

A method for the production of dichloroformoxime is disclosed in which chloropicrin is dissolved in a non-basic aprotic organic solvent together with anhydrous hydrogen chloride, and said chloropicrin is reduced to dichloroformoxime in said solution in the presence of powdered tin acting as both a reactant and catalyst. The reaction is preferably carried out in tetrahydrofuran using at least 15 grams of dissolved hydrogen chloride per 100 grams of solvent and chloropicrin in an amount of at least 50% of the weight of the hydrogen chloride. The powdered tin is used in an amount of at least about 1 mole of tin per mole of chloropicrin, and the reaction temperature is preferably about 0° C.

13 Claims, No Drawings

PRODUCTION OF DICHLOROFORMOXIME

DESCRIPTION

1. Technical Field

This invention relates to a method for the production of dichloroformoxime from chloropicrin.

2. Background Art

As pointed out in U.S. Pat. No. 2,918,418, dichloroformoxime, also known as phosgene oxime, has various utilities, namely: as a military poison gas, in organic synthesis, and as a precursor for the production of hydroxyl amine hydrochloride which is a useful photographic development and also as a reagent in organic synthesis. For this reason it is desirable to be able to produce dichloroformoxime by the reduction of chloropicrin. U.S. Pat. No. 2,918,418 describes the difficulty of doing this, and provides an improved electrolytic process for accomplishing this result. Despite the improvement provided in the patent, the process still involves many steps, an excessive working period and the yields are lower than desired. It is desired to minimize these disadvantages.

DISCLOSURE OF INVENTION

In this invention, chloropicrin (also known as nitrochloroform) is dissolved in a nonbasic aprotic organic solvent together with anhydrous hydrogen chloride, and reduction is then carried out in the presence of powdered tin. Despite the prior experience in which the reductions are carried out in aqueous medium, the process of this invention is preferably carried out in the substantial absence of water. Thus, the solvents used are preferably dried to insure the absence of water, and the hydrogen chloride which is dissolved is anhydrous. Under these conditions it is found that the chloropicrin is reduced to dichloroformoxime with reasonable rapidity and in reasonable yield.

The reaction produces water which is tolerated, but the proportion of water is small so that the medium of reaction is nonaqueous.

While the temperature of the reaction is secondary so long as it is sufficient to enable the reaction to proceed, and not so high as to force the gaseous reactants out of solvent solution, it is preferred to carry out the reaction at about 0° C. for this provides a combination of good reaction speed and good yield. Lower temperatures down to around −20° C. are also useful, and higher temperatures up to around room temperature (25° C.) can also be used, especially when pressure equipment is available, but the yield of the desired oxime product falls off progressively as one goes above 0° C.

The term "aprotic solvent" is a recognized term, and it denotes a solvent which is neither a proton acceptor nor a proton donor. So long as the solvent is aprotic, as noted above, and has the capacity to dissolve hydrogen chloride gas, it can be used herein. Organic solvents generally have the capacity to dissolve hydrogen chloride gas, and can be used if they are inert (aprotic). Those solvents having a greater capacity to dissolve hydrogen chloride gas are preferred because one can react more chloropicrin with a given quantity of solvent. Also, the yield tends to improve as the hydrogen chloride concentration in the solvent increases. Several useful solvents will be illustrated in the examples which follow, it being here noted that tetrahydrofuran is particularly preferred because the yields are better, though why this is so is not clear. It is easier to extract the desired oxime from the solvent when acetonitrile is used.

It is desired to point out that basic solvents, like pyridine, cannot be used because they cause the product to decompose. Acidic or neutral solvents are acceptable.

Proportions are not critical to this invention, but it is preferred to dissolve at least 15 grams of anhydrous hydrogen chloride gas in the solvent per 100 grams thereof in order that the reaction can be carried out in a practical fashion. There is no upper limit to the hydrogen chloride concentration, except as imposed by the solubility of the hydrogen chloride in the selected solvent.

The proportion of chloropicrin which is reacted is desirably at least 50% of the weight of the hydrogen chloride in the solvent solution.

The powdered tin serves as a reactant as well as a reductant, and forms a salt during the reaction which is removed from the product by filtration. It is used in an amount of at least about 1 mole of tin per mole of chloropicrin which is present, preferably in a molar excess of at least 25%.

The invention is illustrated in the following examples.

EXAMPLE 1

Anhydrous hydrogen chloride was bubbled into acetonitrile (300 ml) which was cooled to 0° C. and contained in a 1-liter 3-necked round-bottom flask equipped with a thermometer and mechanical stirrer assembly. The anhydrous hydrogen chloride addition was discontinued after a net gain in weight of 76.1 gms. was obtained. To this solution at 0° C., 31.5 ml. (50.0 gm=0.304 mole) of chloropicrin was added. To this solution, 45.1 gms. (0.38) mole of tin powder was added in increments over a period of 2 hours and 15 minutes while maintaining 0° C. When the tin was first added, the initially colorless solution turned a brilliant blue color, and at the end of the tin addition, the solution was grey in color. The mixture was stirred for an additional hour at 0° C. and white salts were observed to be present in the almost colorless product solution. The salts were removed by filtration. The liquid so-obtained contains solvent, a small amount of water produced by the reaction, and desired product. Distillation under vacuum first removes solvent and water, and then the desired product is removed. This product solidifies in the distillation condenser. When this occurs, a new receiver is placed to receive the material which flows out of the condenser, and the condenser is warmed to melt the product and allow it to flow into the receiver. Two vacuum distillations of the filtrate gave 5.9 gm. (16.8% yield) of the desired dichloroformoxime having a boiling point of 51° C. at 31 mm of mercury pressure. Infrared analysis of the first acetonitrile fraction and the residue in the pot indicated an additional 20% yield of oxime was present and might be recovered.

EXAMPLE 2

The process of Example 1 was repeated using 300 ml. of sodium-dried dioxane in place of the acetonitrile. 71.1 gms of anhydrous hydrogen chloride were dissolved. The appearance and disappearance of the blue color during the course of the reaction was also noted. After filtration from the inorganic salts and two vacuum distillations, 20.6 gms of distillate were obtained having a boiling point of 61° C. at 30 mm. of mercury pressure. Infrared analysis indicated the fraction contained oxime and dioxane, and proton nuclear magnetic resonance indicated 73.1 weight percent of dicloroformoxime in the dioxane solution. The oxime yield was 43.5%.

EXAMPLE 3

The reaction procedure of Example 1 was repeated using 400 ml. of tetrahydrofuran which had been dried and distilled over lithium aluminum hydride in place of the acetonitrile used in Example 1. In this repeat of Example 1, 158.3 gms. of anhydrous hydrogen chloride were dissolved in the tetrahydrofuran. The appearance and disappearance of the blue color during the course of the reaction was noted, and the total reaction time was approximately 6 hours and 45 minutes. After filtration to remove the inorganic salts, the colorless filtrate was concentrated on a rotary film evaporator. Two vacuum distillations gave 26.0 gms. of a fraction boiling at 55°–57° C. at 28 mm. of mercury pressure. Infrared analysis indicated the fraction contained the desired oxime and tetrahydrofuran. With 82.2 weight percent of oxime in the fraction as determined by proton nuclear magnetic resonance, the yield of the desired dichloroformoxime was 61.8%.

In addition to the solvents used in the Examples, benzonitrile was also used as the solvent to see whether aromatic solvents could be used, and good results were again obtained.

It should be noted that the solvents may be recycled and that the tin salts which are removed by filtration are themselves useful by-products, being useful in oil well drilling operations.

What is claimed is:

1. A method for the production of dichloroformoxime comprising dissolving chloropicrin in a nonbasic aprotic organic solvent together with anhydrous hydrogen chloride, and reducing said chloropicrin to dichloroformoxime in said solution in the presence of powdered tin.

2. A method as recited in claim 1 in which said solvent is tetrahydrofuran.

3. A method as recited in claim 1 in which said solvent is acetonitrile.

4. A method as recited in claim 1 in which said reaction is continued until the blue color which appears when said tin is added disappears.

5. A method as recited in claim 1 in which said reaction is carried out at a temperature sufficient to enable the reaction to proceed, and not so high as to force the gaseous reactants out of solvent solution.

6. A method as recited in claim 1 in which said reaction is carried out at a temperature of from about −20° C. up to about 25° C.

7. A method as recited in claim 1 in which said reaction is carried out at a temperature of about 0° C.

8. A method as recited in claim 1 in which said solvent is substantially anhydrous at the start of the reaction.

9. A method as recited in claim 1 in which at least about 15 grams of anhydrous hydrogen chloride is dissolved in said solvent per 100 grams of solvent.

10. A method as recited in claim 1 in which the proportion of chloropicrin which is reacted is at least 50% of the weight of the hydrogen chloride in the solvent solution.

11. A method as recited in claim 10 in which the powdered tin is used in an amount of at least about 1 mole of tin per mole of chloropicrin which is present.

12. A method as recited in claim 10 in which the powdered tin is used in a molar excess of at least 25%.

13. A method as recited in claim 12 in which said reaction is carried out at a temperature of about 0° C.

* * * * *